(12) United States Patent
Jayaram et al.

(10) Patent No.: US 7,507,020 B2
(45) Date of Patent: Mar. 24, 2009

(54) METHOD AND ASSEMBLY FOR ASSESSING RELATIVE DEGRADATION RESISTANCE OF MATERIALS WITH LASER

(75) Inventors: Sheshakamal H. Jayaram, Waterloo (CA); Luiz H. Meyer, Blumenau (BR); Edward A. Cherney, Huntsville (CA)

(73) Assignee: University of Waterloo, Waterloo, ON (CA)

( * ) Notice: Subject to any disclaimer, the term of this patent is extended or adjusted under 35 U.S.C. 154(b) by 0 days.

(21) Appl. No.: 10/981,743

(22) Filed: Nov. 5, 2004

(65) Prior Publication Data

US 2005/0185693 A1     Aug. 25, 2005

Related U.S. Application Data

(60) Provisional application No. 60/517,062, filed on Nov. 5, 2003.

(51) Int. Cl.
  *G01N 25/00* (2006.01)
  *G01N 25/18* (2006.01)
  *G01N 25/20* (2006.01)
  *G01J 5/00* (2006.01)

(52) U.S. Cl. .............................. 374/7; 374/57; 374/44; 374/43; 374/121; 374/161

(58) Field of Classification Search ................... 374/7, 374/44, 45, 57, 121, 161
  See application file for complete search history.

(56) References Cited

U.S. PATENT DOCUMENTS

| | | | | |
|---|---|---|---|---|
| 3,808,439 A * | 4/1974 | Renius | ...................... | 250/334 |
| 5,239,488 A * | 8/1993 | Markham et al. | ............ | 702/135 |
| 5,406,082 A * | 4/1995 | Pearson et al. | ......... | 250/339.11 |
| 6,568,846 B1 | 5/2003 | Cote et al. | | |
| 2003/0202556 A1 * | 10/2003 | Taketoshi et al. | ............. | 374/45 |

OTHER PUBLICATIONS

E.A. Cherney, "Non-Ceramic Insulators—A Simple Design that Requires Careful Analysis", IEEE Electrical Insulation Magazine, vol. 12, No. 3, May/Jun. 1996, pp. 7-15.

C. Tourreil, "Failure Rates of High Voltage Line Insulators", Insulator News and Market Report, May/Jun. 2000, http://www.inmr.com/issues/2000/may_jun/12_Failure_Rates/failure04.htm, 7 pages.

R.S. Gorur, et al., "The Electrical Performance of Polymeric Insulating Materials under Accelerated Aging in a Fog Chamber", IEEE Trans. on Power Delivery, vol. 3, No. 3, Jul. 1988, pp. 1157-1164.

(Continued)

*Primary Examiner*—Gail Verbitsky
*Assistant Examiner*—Mirellys Jagan

(57) ABSTRACT

To assess relative degradation resistance of different materials, one or more samples of each of the materials is irradiated with a beam of laser. The laser is chosen or tuned such that the laser beam has no wavelength sufficient to cause a photochemical reaction in material samples but the degree of irradiation is sufficient to degrade each material. A measure of degradation of each material sample is determined in consequence of the irradiation. The relative degradation resistance of each material is ranked based on these measures of degradation. In one approach, each sample may be irradiated until about the same pre-selected laser energy has been absorbed by the sample. In another approach, each sample may be irradiated for about the same time, while maintaining the irradiated portion of the sample at a same pre-selected temperature.

13 Claims, 1 Drawing Sheet

OTHER PUBLICATIONS

S.H. Kim, et al., "Chemical Changes at the Surface of RTV Silicone Rubber Coatings on Insulators During Dry-Band Arcing", IEEE Trans. on Dielectric and Electrical Insulation, vol. 1, No. 1, Feb. 1994, pp. 106-123.

S. Kumagai, et al., "Tracking and Erosion of HTV Silicone Rubber and Suppression Mechanism of ATH", IEEE Trans. on Dielectrics and Electrical Insulation, vol. 8, No. 2, Apr. 2001, pp. 203-211.

S. Kumagai, et al., "Tracking and Erosion of HTV Silicone Rubbers of Different Thickness", IEEE Trans. on Dielectrics and Electrical Insulation, vol. 8, No. 4, Aug. 2001, pp. 673-678.

T.G. Gustavsson, et al., "Aging of Silicone Rubber under AC or DC Voltages in a Coastal Environment", IEEE Trans. on Dielectrics and Electrical Insulation, vol. 8, No. 6, Dec. 2001, pp. 1029-1039.

J. Mackevich, et al., "Polymer Outdoor Insulating Materials Part II: Material Considerations", IEEE DEIS Electrical Insulation Magazine; Jul./Aug. 1997, vol. 13, No. 4, pp. 10-16.

S. Simmons, et al., "Polymer Outdoor Insulating Materials Part III: Silicone Elastomer Considerations", IEEE DEIS Electrical Insulation Magazine, Sep./Oct. 1997, vol. 13, No. 5, pp. 25-32.

Y. Koshino, et al., "Deterioration of Silicone Rubber for Polymer Insulators by Corona Discharge and Effect of Fillers", IEEE Conference on Electrical Insulation and Dielectric Phenomena, Atlanta, GA, Oct. 25-28, 1998, vol. 1, pp. 72-79.

L. Meyer, et al., "Thermal Characteristics of Silicone Rubber Filled with ATH and Silica under Laser Heating", Conference on Electrical Insulation and Dielectric Phenomena, Cancun, Mexico, Oct. 20-24, 2002, pp. 848-852.

K. Takashima, et al., "Space- and surface-charge behaviour analysis of plasma pre-processed dielectric thin films". IAS Annual Meeting, New Orleans, USA, Oct. 5-9, 1997, IEEE Trans. on Industry Applications, vol. 35, No. 5, Sep./Oct. 1999, pp. 1192-1197.

A.H. Ei-Hag, et al., "Fundamental and Low Frequency Harmonic Components of Leakage Current as a Diagnostic Tool to Study Aging of RTV and HTV Silicone Rubber in Salt Fog" IEEE Trans. on Dielectrics and Electrical Insulation, vol. 10, No. 1, Feb. 2003, pp. 128-136.

R.S. Gorur, et al., "The AC and DC Performance of Polymeric Insulating Materials unde Accerlated Aging in a Fog Chamber", IEEE Trans. on Power Delivery, vol. 3, No. 4, Oct. 1988, pp. 1892-1902.

ASTM-D2303, "Standard Test Method for Liquid-Contaminant, Inclined-Plane Tracking and Erosion of Insulating Materials", pp. 504-513.

I.L. Hosier, et al., "Simulation of Surface Discharge Damage in Polymers, Using Laser Ablation and Computational Modelling Techniques", Proceedings of the International Conference on Dielectric and Insulation, Budapest, Sep. 10-13, 1997, G. Woynarovich Editors, pp. 349-352.

A.S. Vaughan, "Polymer surfaces: designing materials to prevent or withstand discharge activity", 1997 The Institute of Electrical Engineers, pp. 9/1-3, London, UK.

S.-H. Kim, et al., "Thermal Characteristics of RTV Silicone Rubber Coatings as a Function of Filter Level", Conference on Electrical Insulation and Dielectric Phenomena, Victoria, BC, Canada, Oct. 18-21, 1992, pp. 713-718.

* cited by examiner

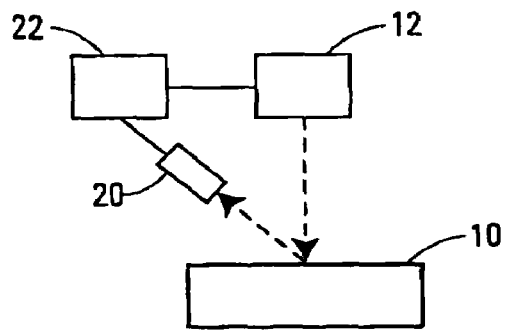
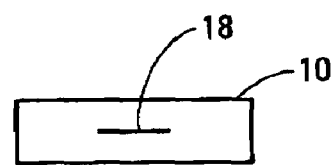
FIG. 1
FIG. 4
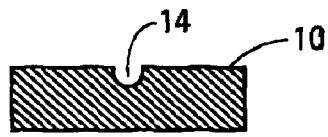
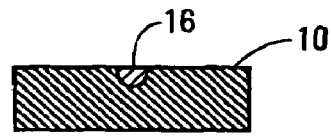
FIG. 2A  FIG. 2B  FIG. 2C
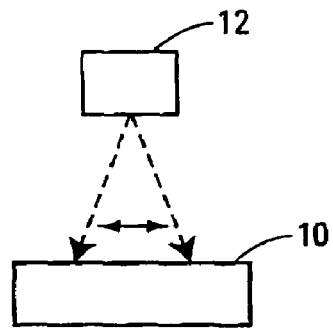
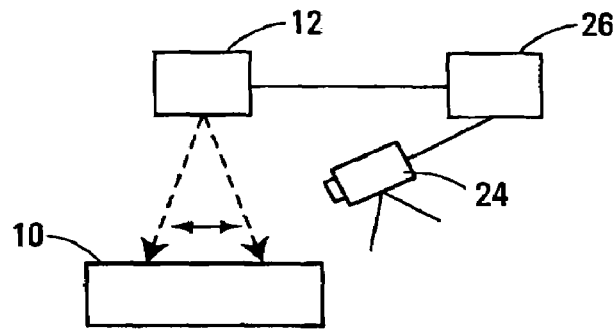
FIG. 3  FIG. 5

METHOD AND ASSEMBLY FOR ASSESSING RELATIVE DEGRADATION RESISTANCE OF MATERIALS WITH LASER

CROSS-REFERENCE TO RELATED APPLICATIONS

This application claims priority from the U.S. provisional application No. 60/517,062, entitled "METHOD, SYSTEM AND APPARATUS FOR EVALUATION OF EROSION RESISTANCE OF INSULATING MATERIALS" and filed Nov. 5, 2003, which is incorporated herein by reference.

FIELD OF THE INVENTION

The present invention relates generally to material analysis, and more particularly to methods and assemblies for assessing relative degradation resistance of materials such as organic insulating materials.

BACKGROUND OF THE INVENTION

Heat has been identified as a major cause for degradation of materials, such as insulating materials. For example, heat can cause erosion, i.e. loss of material. In high tension power systems, heat generated by dry band arcing is the principal cause of degradation of the insulation on the surface of insulators. (Secondary factors contributing to degradation include pollution, moisture, ultraviolet (UV) exposure and ozone.) Heavily degraded insulation in high tension power systems presents hazards, such as the possibility of a ground fault. Therefore, in developing and testing new materials such as insulating materials, it is often important to assess their relative heat resistance.

Conventional methods for ranking different insulating materials typically employ the Inclined-Plane Test (IPT) technique. For example, both the American Society for Testing and Materials (ASTM) and International Electrotechnical Commission (IEC) have established standard IPT methods, such as the ASTM D2303 method and the IEC 60587 method. In an IPT method, a flat test surface of the sample is oriented at an angle of 45° to a horizontal plane. A test solution containing contaminant is allowed to flow along a path down the test surface. A high voltage is applied across two electrodes disposed at two ends of the path, typically spaced apart by two inches. The electrical current between the electrodes generates heat, which causes degradation of the sample material at the surface by erosion and/or tracking. A track is a conductive path that may develop if the degradation residue contains a conductive material, typically free carbon. The length of a track on a sample as a function of time is monitored. In a first test, if a track has not developed, or has not developed to a pre-determined length, such as one inch, within a pre-determined time period, such as one hour, the applied voltage is increased. In a second test, the time to develop a track of specified length at a specified voltage is measured. The materials are then ranked according to their rates of track growth as measured by the noted tests.

The IPT technique has a few shortcomings. For example, it takes a long time to conduct an IPT test: a typical IPT test for one sample will last at least 10 hours. Indeed, to measure erosion, the ASTM D2303 standard recommends 24 to 48 hours of test time for each sample. It is difficult to provide the same amount energy to different samples in IPT tests, which reduces the reliability of the test. The results of IPT tests are also affected by many environmental and other factors, which may not be controllable and can also negatively affect the reproducibility of an IPT test. In addition, tests often have to be repeated due to the uncertainty in the test results, leading to increased testing time.

It has been suggested that an infrared laser can be used as an energy source to quickly and cheaply rank different materials, see A. S. Vaughan, "Polymer surfaces: designing materials to prevent or withstand discharge activity," in *Proceedings of Surface Phenomena Affecting Insulator performance*, Ref. No. 1998/235, (1998), pp. 9/1-9/3 ["Vaughan"]. It has been suggested that the erosion damage caused by irradiation of an infrared laser could be quantified by direct measurement of the consequent pit depth. In one reported procedure, maximum pit depths were measured optically using a microscope, see I. L. Hosier et al., "Simulations of surface discharge damage in polymers using laser ablation and computational modelling techniques", in *Proceedings of International conference on Dielectrics and Insulation*, G. Woynarovich ed., (1997), pp. 349-352 ["Hosier"]. However, the measured pit depths do not always accurately reflect the ranking of heat resistance of different materials. Hence, this method taught by Hosier is not reliable in many cases.

Therefore, there is a need for a fast, efficient, reliable, and inexpensive method or assembly for assessing relative degradation resistance of materials.

SUMMARY OF THE INVENTION

To assess relative degradation resistance of different materials, one or more samples of each of the materials is irradiated with a beam of laser. The laser is chosen or tuned such that the laser beam has no wavelength sufficient to cause a photochemical reaction in material samples but the degree of irradiation is sufficient to degrade each material. A measure of degradation of each material sample is determined in consequence of the irradiation. The relative degradation resistance of each material is ranked based on these measures of degradation. In one approach, each sample may be irradiated until about the same pre-selected laser energy has been absorbed by the sample. In another approach, each sample may be irradiated for about the same time, while maintaining the irradiated portion of the sample at a same pre-selected temperature.

Therefore, in accordance with an aspect of the present invention, there is provided a method for assessing relative heat resistance of different materials, comprising: selecting a laser energy quantity sufficient to erode each of the different materials; for each sample of at least one sample of each material, irradiating the sample with a beam of a laser such that about the energy quantity is absorbed by the sample, the beam having no wavelength sufficient to cause a photochemical reaction in the sample; and determining a measure of erosion of material from the sample in consequence of the irradiating; and ranking relative heat resistance of each material based on the measure of erosion of material from each the sample.

In accordance with another aspect of the present invention, there is provided a method for assessing relative heat resistance of different materials, comprising: selecting a temperature which, over a given time, is sufficient to erode each of the different materials; for each sample of at least one sample of each material, irradiating a portion of the sample with a beam of a laser such that the portion of the sample is maintained at about the temperature for about the given time, the beam having no wavelength sufficient to cause a photochemical reaction in the sample; and determining a measure of erosion of material of the sample in consequence of the irradiating;

and ranking relative heat resistance of each material based on the measure of erosion of material from each sample.

In accordance with another aspect of the present invention, there is provided an assembly for use in assessing relative heat resistance of different materials. The assembly comprises an infrared laser for irradiating material samples; a laser power detector for measuring power reflected from samples; a processor for determining an energy absorbed by a sample and for terminating the irradiation upon the energy absorbed by the sample reaching a pre-defined value.

In accordance with another aspect of the present invention, there is provided an assembly for use in assessing relative heat resistance of different materials. The assembly comprises an infrared laser for irradiating material samples; a temperature sensor for measuring a temperature on a surface of a sample being irradiated; and a processor for controlling output power of the laser so as to maintain the surface temperature at about a pre-defined temperature and for terminating the irradiation after a pre-defined time.

In accordance with another aspect of the present invention, there is provided a method for assessing relative degradation resistance of different materials, comprising: selecting a laser energy quantity sufficient to degrade each of the different materials; for each sample of at least one sample of each material, irradiating the sample with a beam of a laser such that about the energy quantity is absorbed by the sample, the beam having no wavelength sufficient to cause a photochemical reaction in the sample; and determining a measure of degradation of material from the sample in consequence of the irradiating; and ranking relative degradation resistance of each material based on the measure of degradation from each the sample.

In accordance with another aspect of the present invention, there is provided a method for assessing relative degradation resistance of different materials, comprising: selecting a temperature which, over a given time, is sufficient to degrade each of the different materials; for each sample of at least one sample of each material, irradiating a portion of the sample with a beam of a laser such that the portion of the sample is maintained at about the temperature for about the given time, the beam having no wavelength sufficient to cause a photochemical reaction in the sample; and determining a measure of degradation of material of the sample in consequence of the irradiating; and ranking relative degradation resistance of each material based on the measure of degradation of material from each the sample.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures, which illustrate exemplary embodiments of the invention,

FIG. 1 is a schematic front plan view of a setup for irradiating a sample with a laser light and detecting the reflected laser power;

FIG. 2A is a front sectional view of the sample of FIG. 1 before being irradiated;

FIG. 2B is a front sectional view of the sample of FIG. 1 after being irradiated, showing a lost volume;

FIG. 2C is a front sectional view of the sample of FIG. 2B with the lost volume being filled with a material;

FIG. 3 is similar to FIG. 1 but illustrates scanning movement of the laser light;

FIG. 4 is a top plan view of the sample in FIG. 3 after being irradiated; and

FIG. 5 is a schematic front plan view of a setup for irradiating a sample with a laser light and sensing the sample surface temperature.

DETAILED DESCRIPTION

An exemplary embodiment of the present invention is a method of assessing relative heat resistance of different materials, such as electrical insulating materials or materials used to insulate outdoor high tension wires. Heat resistance is the ability of a material in resisting a heat-induced loss of material mass or other heat-induced degradation.

As illustrated in FIG. 1, for each material, at least one sample 10 is irradiated with a laser beam (as indicated by the downward arrow) using a laser source 12. The laser is chosen or tuned so that the laser beam has no wavelength sufficient to cause a photochemical reaction in sample 10. Laser energy absorbed by sample 10 thus generates heat. Sample 10 is irradiated for a sufficient time so that a pre-selected energy quantity ($E_\alpha$) is absorbed by sample 10, which generates enough local heat in sample 10 to cause measurable degradation such as loss of sample mass. The laser beam may be focused on to sample 10 by one or more focusing lens (not shown) and may pass through a filter (not shown) for frequency attenuation.

As can be understood, if there is no transmitted light, the power absorbed ($P_a$) by sample 10 can be calculated from the incident laser power ($P_i$) and the reflected laser power ($P_r$),:

$$P_a = P_i - P_r. \quad (1)$$

A laser power detector 20 may be used to detect the reflected laser power. Detector 20 can be any suitable laser power detector known to persons skilled in the art. Such detectors are commonly used in the art and are readily available. For example, an infrared spectrometer or a laser power meter may be used as detector 20. An exemplary suitable spectrometer is MS127i™ Imaging Spectrograph, model 77480, from Oriel Instruments.

A processor 22 can be connected to laser source 12 and detector 20 for data processing and control. Processor 22 can process the detected signal or data to determine the amount of energy absorbed by sample 10. When the absorbed energy reaches the pre-selected quantity, processor 22 can terminate the irradiation. For example, once $P_a$ is determined for a given $P_i$, laser source 12 may operate at the given $P_i$ for a time t such that $P_a \times t = E_\alpha$. Processor 22 can include a microprocessor and other electronic devices such as memories, communication devices and the like, and may also include softwares for control and data processing. Alternatively, $P_a$ may be noted by an operator and $E_\alpha$ calculated, then laser source 12 can simply be manually turned off at the appropriate time.

As illustrated in FIGS. 2A to 2B, wherein FIG. 2A shows a cross-section of sample 10 before irradiation and FIG. 2B shows a cross-section of sample 10 after irradiation, a void 14 is created in sample 10 due to lost mass as a result of irradiation by the laser beam. Void 14 is mainly the result of erosion due to local heat generated by the laser beam. The volume of void 14 substantially equals the lost volume of sample 10 in consequence of the laser irradiation. Void 14 should be sufficiently large to allow accurate measurement of its volume. Roughly semi-spherical voids having an average diameter of about 2 mm and a depth of about 0.8 mm have been found adequate.

This lost volume due to irradiation is then determined.

For instance, the lost volume may be determined as follows. First, the surface of sample 10 is cleaned to remove any residue or debris in void 14 resulting from the irradiation, such as loose particles produced by laser irradiation. Residues or debris can accrue particularly when the sample material (such as an insulating material) includes an organic binder and an inorganic filler. An inorganic filler is usually substantially more heat resistant than an organic binder and so can survive irradiation as a residue. The surface of sample 10 can be cleaned by, e.g., brushing.

Void 14 is then filled with a plastic material such as a putty 16 of known density (d), as illustrated in FIG. 2C.

Putty 16 is then removed and weighed, such as on a balance. The lost volume (V) can be calculated from the weight (w) of filler 16 as V=w/d. Putty 16 can be formed from any plastic material that is suitable for filling void 14 and that can be subsequently removed. As can be understood, a high density putty material may be advantageous. For example, suitable putty is sold under the trade name DUXSEAL™.

The lost volume may also be determined in any other suitable manner known to persons skilled in the art. For example, in some applications, lost volumes may be determined by weighing each sample before and after irradiation and calculating the lost volume from the weight difference and the density of the sample material. However, this way of determining lost volume may not be accurate if the lost mass is only a small fraction of the total mass of the sample. As a further example, the lost volume could be determined by optical measurements of the dimensions of (or at least the depth of) void 14.

The above procedure is repeated for each material to be assessed. While the same quantity of energy is absorbed by each sample, different lost volumes, V, may be obtained for samples of different materials. Indeed, there will even be some variation in the volumes lost between different samples of the same material due to differences between samples of the same material which may exist because of the manufacturing tolerances in the fabrication of the material. Therefore, to obtain more accurate results, multiple samples may be tested for each material and the average lost volume for the material can be used for ranking the heat resistance of the material.

The relative heat resistance of each material is then ranked based on the (average) lost volume V of its sample(s). A material displaying a higher lost volume is ranked lower than a material displaying a lower lost volume. Thus, assuming materials M1, M2, and M3 have corresponding lost volumes V1, V2 and V3, wherein V1>V3>V2, the materials are ranked as M2, M3, and M1 in order of their relative heat resistance.

In this method, sample 10 may have any suitable shape or size that allows the creation of a large enough void. For instance, sample 10 may be generally rectangular, and may measure, for example, 10 mm×5 mm×7 mm. It may be advantageous if sample 10 has a smooth flat surface for receiving laser irradiation, as can be appreciated by a person of skill in the art. Further, the sample surface may be cleaned before testing.

Laser source 12 may be placed at any suitable distance from sample 10. For example, a distance of 50 mm maybe adequate. Longer or shorter distances may also be adequate in different applications. As depicted in FIG. 1, the laser beam is incident on sample 10 at a substantially right angle, but the angle can be smaller as long as sufficient energy is imparted to sample 10 within a limited area. The laser beam may be aimed at a fixed point on sample 10. Alternatively, the laser beam may be scanned along a pre-determined path on sample 10. For example, as shown in FIGS. 3 and 4, the beam may be scanned back-and-forth along line 18 on sample 10, the benefit of which will be discussed below.

Laser source 12 can be any suitable laser source for generating a laser beam and for imparting energy to sample 10 in a controlled manner to produce heat in a limited area of sample 10, as described herein. For example, laser source 12 may be an infrared semiconductor laser source operated in continuous mode or pulsed mode.

The laser beam should have a suitable wavelength or bandwidth. The wavelength should be such that the energy quantum of the laser beam is sufficiently small so as not to cause a photochemical reaction, i.e. directly break or form chemical bonds in sample 10. As can be appreciated, the suitable wavelength may vary depending on the sample materials. In this regard, wavelengths in the infrared range may be suitable. A wavelength in the near infrared range, such as about 808 nm, has been found suitable for testing inorganic polymers such as silicone rubber materials. At such a wavelength, the energy quantum of the laser beam is not sufficient to cause a photochemical reaction in sample 10 but is sufficient to cause molecular vibration, which in turn generates heat. Generally, a wavelength in the range of about 700 nm to about 900 nm may be suitable. Visible laser may also be suitable in some applications. Generally speaking, wavelengths in the Ultra Violet (UV) range should be avoided as a UV laser beam can cause photochemical reactions in many materials.

Laser source 12 should be operated at a suitable power level to provide an adequate power density (i.e. power per unit surface area). The power density is too low if the laser beam cannot produce sufficient heat in sample 10 to cause measurable erosion of sample 10 within a given time period, such as on the order of tens of seconds. For example, if the laser power density is below a certain value and heat is generated slowly, a large portion of the generated heat may disperse through thermal conduction, into regions away from the surface. As a result, the tests may take a long time to complete and may not give accurate results. On the other hand, the power density is too high if sample 10 is significantly damaged by chemical or physical processes other than those resulting from heating. Again, the consequence would be less accurate results. Further, a through-hole may be created in sample 10 if the power density is too high. Depending on the sample material, the mode of operation and the laser beam diameter, the output power density of laser source 12 may vary. With a laser beam diameter of about 2 mm, an output power between 6 to 8 W may be suitable for silicone rubber, and output power of about 3.5 W may be suitable for organic materials.

The output power of laser source 12 may be constant or varying during each irradiation. However, it can be advantageous to operate laser source 12 at a substantially constant power level for each one of the different samples to be assessed. Given a pre-selected energy quantity to be absorbed by each sample 10 and the absorption power ($P_a$) for the sample, the length of time needed for each irradiation can be readily determined, as described earlier.

As can be appreciated, it is not necessary, and is often impossible in practice, to impart exactly the same amount of energy to each sample 10. Thus, it should be understood that a pre-selected energy quantity is considered herein as being absorbed by sample 10 when sample 10 has absorbed an energy substantially equal to the pre-selected energy quantity, to the extent that the difference in energy is negligible or inconsequential to the ranking of heat resistance of different materials. The tolerance can vary depending on the particular application and the accuracy required. For example, a 10% tolerance may be tolerable in many applications.

It can also be appreciated that many materials are not homogeneous, in that different regions in a sample may have different chemical or physical properties. In such a situation, scanning the laser beam on sample 10 along a pre-determined path will provide more accurate results as the eroded volume over a larger region is measured.

Scanning along a path may also be advantageous where there is a significant amount of filer in a material. Specifically, residuals (such as freed fillers) produced by irradiation, if produced in sufficient quantity, can prevent transmission of further radiation into a sample. In such a case, only a shallow layer of the sample may be lost due to irradiation. For such a material, scanning can be advantageous as a shallow trench in the sample would provide a sufficient lost volume for comparison with other samples.

In another embodiment of the invention, instead of imparting the same energy to different samples, the laser output power is adjusted so that a portion of the sample is maintained at about a pre-selected temperature for a given time.

An exemplary setup for this constant temperature method is illustrated in FIG. 5. In this method, a laser beam (again, having no wavelength sufficient to cause a photochemical reaction in the material samples) from laser source 12 irradiates a portion of sample 10, such as by scanning along a line as shown in FIGS. 3 and 4, to heat the portion to a constant temperature T for time t. The laser beam may also move along any other convenient path. The temperature T and time t are pre-selected. Temperature T should be attainable on all samples by imparting laser energy at an appropriate power density with laser source 12, and should be sufficient to create measurable degradation, such as erosion, in each material over the pre-selected time t. Temperature T may be selected depending on the materials to be ranked. For certain materials, a few hundred degrees Celsius may be suitable. The time t can vary depend on the application and may be on the order of tens of seconds.

A temperature sensor 24 is used to sense the surface temperature at the scanned portion. Temperature sensor 24 can be any suitable temperature sensing device, such as a remote sensing device including infrared cameras. Suitable temperature sensors are commonly used in the art and are readily available. For example, a Forward Looking Infrared (FLIR) device such as a FLIR-SC500 infrared camera may be used as sensor 24.

A processor 26 is connected to laser source 12 and sensor 24 for adjusting the output power of laser source 12 to maintain the surface temperature at about the pre-selected T for a time t. As in processor 22, processor 26 can include a microprocessor and other electronic devices such as memories, communication devices and the like, and may also include software for control and data processing.

After irradiation, the lost volume of each sample is again determined as described above. The heat resistance of the materials is then ranked accordingly, as described above.

The constant temperature method is advantageous because it is easy to perform. It is no longer necessary to monitor or calibrate for reflected laser energy or power. The only physical parameter to be monitored and maintained is the surface temperature.

As now can be appreciated, since an about equal laser energy is absorbed by different samples, or a constant temperature is maintained at a portion of different samples for about a same time, despite varying environmental factors, the ranking results can be reliable and reproducible.

The amount of energy imparted in a test that accords to embodiments of the present invention can be much smaller than what is required in a typical Inclined-Plane Test (IPT). For example, it has been shown that about 195 J of energy provided to each sample is sufficient for ranking silicone rubber materials using the subject laser technique, which is merely about one percent of the energy consumed in a typical IPT test (about 19 kJ).

As can be appreciated, the ranking methods taught herein can be completed in a relative short period of time. A test for one sample can be completed within a few minutes. In comparison, a typical IPT test lasts up to 48 hours.

As will be understood by those skilled in the art, the subject invention is suited to rank organic materials, as such materials will degrade by laser energy.

As can be understood, since it has been shown that heat is the primary cause of erosion, the relative erosion resistance of different materials can also be accurately assessed by imparting heat to material samples using the subject laser ranking method, without subjecting the samples to electrical current or discharge as is the case in an IPT.

While the laser energy directed at a material sample has been described as eroding the material of the sample, it will be appreciated that for certain materials, the laser energy may cause other types of degradation of the material. For example, the laser energy may cause a change in the chemical composition of the material, or may cause a physical change such as densifying or embrittling the material. Each of these other types of degradation may be measured in a conventional fashion, using known suitable instrumentation and techniques which are readily available and understood by persons skilled in the art. For example, surface analysis or characterization techniques and instruments may be used, including Fourier Transform Infrared (FTIR) spectroscopy, X-ray analysis, surface reflectance analysis, scanning electron microscopy (SEM), X-ray photoelectron spectroscopy (XPS), and the like. Thus, it will be appreciated that in its most general form, the subject invention allows for the ranking of a measure of degradation of a material. The measure of degradation can be determined by various commonly known methods of analysis.

Other features, benefits and advantages of the present invention not expressly mentioned above can be understood from this description and the drawings by those skilled in the art.

Of course, the above described embodiments are intended to be illustrative only and in no way limiting. The described embodiments are susceptible to many modifications of form, arrangement of parts, details and order of operation. The invention, rather, is intended to encompass all such modification within its scope, as defined by the claims.

What is claimed is:

1. A method for assessing relative heat resistance of different materials, comprising:
   selecting a laser energy quantity sufficient to erode each of said different materials;
   for each sample of at least one sample of each material,
      irradiating said sample with a beam of a laser such that said sample is eroded by said irradiating, said beam having no wavelength sufficient to cause a photochemical reaction in said sample;
      determining that about said energy quantity is absorbed by said sample; and
      determining a measure of erosion of material from said sample in consequence of said irradiating; and
   ranking relative heat resistance of each material based on said measure of erosion of material from each said sample, wherein said determining that about said energy quantity is absorbed by said sample comprises measuring energy supplied by said irradiating and energy reflected from said sample.

2. The method of claim 1 wherein said determining a measure of erosion comprises, for a given sample:
filling a void consequent upon said irradiating with a plastic material of known density; and
removing and weighing said plastic material.

3. The method of claim 1 wherein each said material is an insulating material having an organic binder and an inorganic filler, and further comprising removing any inorganic filler freed from said binder by said irradiating before said determining a measure of erosion.

4. The method of claim 1, wherein each said material includes an organic material.

5. The method of claim 1 wherein said irradiating is irradiating with an infrared laser.

6. The method of claim 5 wherein said irradiating is irradiating with a laser having a wavelength of between 700 and 900 nm.

7. A method for assessing relative heat resistance of different materials, comprising:
selecting a laser energy quantity sufficient to erode each of said different materials;
for each sample of at least one sample of each material,
irradiating said sample with a beam of a laser such that said sample is eroded by said irradiating, said beam having no wavelength sufficient to cause a photochemical reaction in said sample;
determining that about said energy quantity is absorbed by said sample; and
determining a measure of erosion of material from said sample in consequence of said irradiating; and
ranking relative heat resistance of each material based on said measure of erosion of material from each said sample,
wherein said irradiating comprises scanning said laser beam on each said sample along a pre-determined path.

8. The method of claim 7 wherein said scanning along a pre-determined path comprises scanning back-and-forth along a line.

9. A method for assessing relative heat resistance of different materials, comprising:
selecting a laser energy quantity sufficient to erode each of said different materials;
for each sample of at least one sample of each material,
irradiating said sample with a beam of a laser such that said sample is eroded by said irradiating, said beam having no wavelength sufficient to cause a photochemical reaction in said sample;
determining that about said energy quantity is absorbed by said sample; and
determining a measure of erosion of material from said sample in consequence of said irradiating; and
ranking relative heat resistance of each material based on said measure of erosion of material from each said sample,
wherein a plurality of samples of each material are irradiated and, for samples of a given material, determining an average measure of erosion, and using said average measure of erosion in ranking relative heat resistance of said given material.

10. A method for assessing relative degradation resistance of different materials, comprising:
selecting a laser energy quantity sufficient to degrade each of said different materials;
for each sample of at least one sample of each material,
irradiating said sample with a beam of a laser such that said sample is degraded by said irradiating, said beam having no wavelength sufficient to cause a photochemical reaction in said sample;
determining that about said energy quantity is absorbed by said sample; and
determining a measure of degradation of material from said sample in consequence of said irradiating; and
ranking relative degradation resistance of each material based on said measure of degradation from each said sample,
wherein said determining that about said energy quantity is absorbed by said sample comprises measuring energy supplied by said irradiating and energy reflected from said sample.

11. A method for facilitating assessment of relative heat resistance of different materials, comprising:
for each sample of at least one sample of each material:
irradiating said sample with a source of radiation such that said sample is eroded or degraded by said irradiating;
measuring reflected irradiation power from said sample in response to said irradiating with a power detector;
measuring a quantity of energy absorbed by said sample due to said irradiating based on output from said detector and from said source of irradiation;
terminating said irradiating when said quantity of absorbed energy reaches a pre-selected energy value; and
determining a change in said sample caused by said irradiating, as a basis for assessing said relative heat resistance of said different materials.

12. The method of claim 11, wherein said sample has a thickness of more than about 0.8 mm.

13. A method for facilitating assessment of relative heat resistance of different materials, comprising:
for each sample of at least one sample of each material:
irradiating said sample with a beam of a laser such that said sample is eroded or degraded by said irradiating, said beam having no wavelength sufficient to cause a photochemical reaction in said sample;
determining a parameter value associated with said sample using a parameter detector;
terminating said irradiating after a time period based, at least in part, on said determining;
wherein said parameter value associated with said sample is energy absorbed by said sample and wherein said parameter detector is a power detector,
wherein said determining said parameter value comprises measuring energy supplied by said irradiating and energy reflected from said sample.

* * * * *